United States Patent [19]

Long

[11] 4,237,281
[45] Dec. 2, 1980

[54] DYESTUFFS CONTAINING AMINO OR IMINO GROUPS

[75] Inventor: William E. Long, Brentwood, England

[73] Assignee: Ciba-Geigy Aktiengesellschaft, Basel, Switzerland

[21] Appl. No.: 14,780

[22] Filed: Feb. 23, 1979

[30] Foreign Application Priority Data

Oct. 13, 1978 [GB] United Kingdom ............... 40401/78

[51] Int. Cl.³ .................. C07D 241/46; C07D 265/38; C07D 279/36
[52] U.S. Cl. .................................. 544/99; 260/345.3; 542/403; 542/404; 542/415; 544/37; 544/103; 544/348; 546/104; 549/16
[58] Field of Search .................... 544/37, 99, 103, 348; 542/403, 404, 415

[56] References Cited

U.S. PATENT DOCUMENTS

| | | | |
|---|---|---|---|
| 366,639 | 7/1867 | Ullrich | 544/37 |
| 2,783,227 | 2/1957 | Adams et al. | 544/37 |
| 3,873,340 | 3/1975 | Miyazawa et al. | 544/103 X |
| 3,951,974 | 4/1976 | Crabtree | 544/348 |
| 3,972,879 | 8/1976 | Psaar | 544/103 |
| 4,141,688 | 2/1979 | Morris et al. | 544/103 X |

*Primary Examiner*—Richard Raymond
*Attorney, Agent, or Firm*—Sprung, Felfe, Horn, Lynch & Kramer

[57] ABSTRACT

Novel dyestuffs containing amino or imino groups and their preparation are provided.

These dyestuffs have the general formula

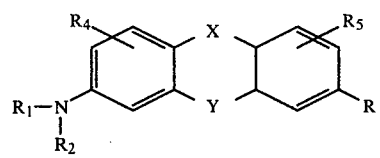

wherein R is $-N(R_3)CH_2-Z$ or $-N=CH-Z$, X is N or $CR_6$ where $R_6$ is a hydrogen atom or an optionally substituted alkyl or aryl group, Y is $S^{\oplus}$, $O^{\oplus}$, N or $N^{\oplus}R_7$ where $R_7$ is a hydrogen atom or an optionally substituted alkyl or aryl group, $R_1$, $R_1$ and $R_2$ each represent a hydrogen atom or an alkyl group having from 1 to 4 carbon atoms, or $R_1$ and $R_2$ together with the nitrogen atom complete a heterocyclic ring, or one of $R_1$ and $R_2$ can be hydrogen and the other of $R_1$ and $R_2$ can be aryl, Z is a group which comprises both an activating group which contains at least one double bond system and also a ballasting group and $R_4$ and $R_5$ each represent optional substituents or form an annelated benzene ring. The new dyestuffs are useful in the photographic field especially in the photographic dye diffusion transfer process for the production of photographic images.

9 Claims, No Drawings

DYESTUFFS CONTAINING AMINO OR IMINO GROUPS

This invention relates to novel chemical compounds and to a method of preparing them.

According to the present invention there are provided compounds of the general formula

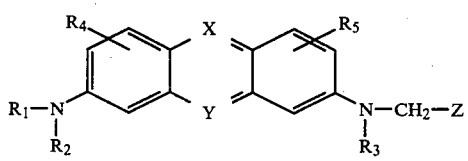

or of the general formula

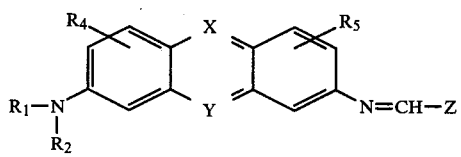

wherein X is N or $CR_6$ where $R_6$ is a hydrogen atom or an optionally substituted alkyl or aryl group, Y is $S^⊕$, $O^⊕$, N or $N^⊕R_7$ where $R_7$ is a hydrogen atom or an optionally substituted alkyl or aryl group, $R_1$, $R_2$ and $R_3$ each represent a hydrogen atom or an alkyl group having from 1 to 4 carbon atoms, or $R_2$ and $R_3$ together with the nitrogen atom complete a heterocyclic ring, or one of $R_2$ and $R_3$ can be hydrogen and the other of $R_2$ and $R_3$ can be aryl, Z is a group which comprises both an activating group (as hereinafter defined) which contains at least one double bond system, and also a ballasting group, and $R_4$ and $R_5$ each represent optional substituents or form an annelated benzene ring.

Examples of such further substituents are alkyl of 1 to 4 carbon atoms, particularly methyl, amino and halogen atoms (fluorine, chlorine, bromine).

$R_6$ is preferably hydrogen, alkyl of 1 to 4 carbon atoms, phenyl or phenyl substituted by alkyl of 1 to 4 carbon atoms, halogen, hydroxy or carboxyl.

Preferably $R_7$ has the meaning indicated for $R_6$ except hydrogen. Preferably $R_1$ and $R_2$ are hydrogen, methyl or ethyl and $R_3$ is hydrogen. $R_2$ and $R_3$ together with the nitrogen atom can complete a heterocyclic ring, preferably a 5- or 6- membered heterocyclic ring or one of $R_2$ and $R_3$ can be hydrogen and the other one can be phenyl.

The compounds of formula (2) are the partially oxidised compounds of formula (1).

By activating group is meant a group which activates the $-NR_3-CH_2-$ or $-N=CH-$ bond and renders it more susceptible to reductive cleavage. Preferably this is an electron-with-drawing group.

Examples of suitable activating groups which contain a double bond system are aromatic rings and groups which contain a carbonyl group.

A particularly useful group Z is the group of the general formula

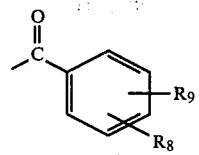

where $R_8$ comprises a ballasting group containing at least 10 carbon atoms and $R_9$ represents a substituent or is preferably hydrogen.

The ballasting groups may be for example alkyl or alkoxy of 10 to 24, preferably alkoxy of 14 to 18 carbon atoms.

Another useful group Z is of the general formula

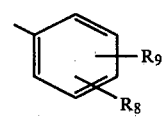

where $R_8$ and $R_9$ have the meanings assigned to them above.

A further useful group Z is of the general formula

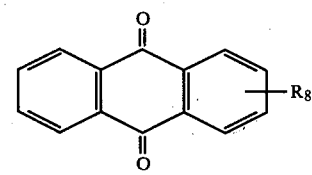

where $R_8$ has the meaning assigned to it above.

Compounds of formula (1) may be prepared by treating a dye of formula

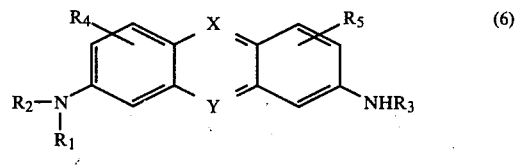

with a base and a suitable alkylating agent of formula

where A is a leaving group and X, Y. Z, $R_1$, $R_2$, $R_3$, $R_4$ and $R_5$ have the meanings assigned to them above. An example of a leaving group is halogen, especially Br.

Compounds of formula (2) may be made by condensing a dye of formula

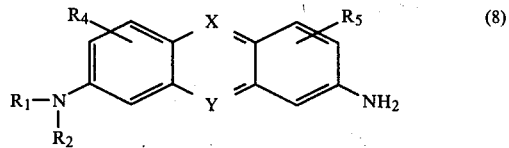

where X, Y, $R_1$, $R_2$, $R_4$ and $R_5$ have the meanings assigned to them above with a substituted aldehyde of formula Z-CHO where Z has the meaning assigned to it above.

When X is N and Y is O⊕ the compounds of formula (1) are oxazine compounds. Particularly useful dyes are of formula

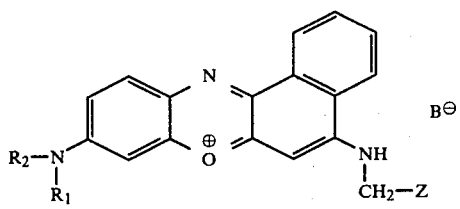
(9)

or when partially oxidised of the formula

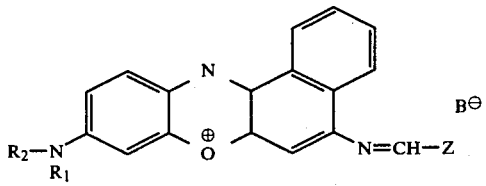
(10)

wherein $R_1$, $R_2$ and Z have the meanings indicated above and B⊖ is an anion such as an halide, for example chloride or bromide. An example of such an oxazine compound is the compound of formula

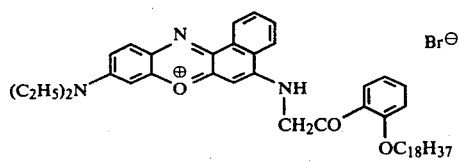
(11)

An oxazine compound of formula (2) is the compound of formula

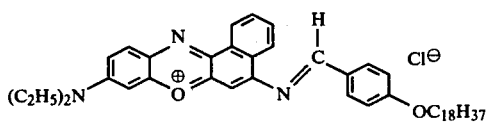
(12)

Compounds of formula (1) wherein X is N and Y is $NR_7⊕$ are phenazine dyes. Particularly useful phenazine compounds of formula (1) are the dyes of formula

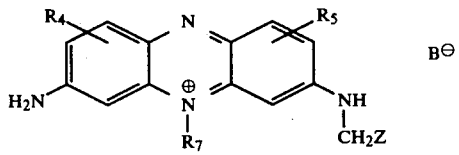
(13)

or when partially oxidised of the formula

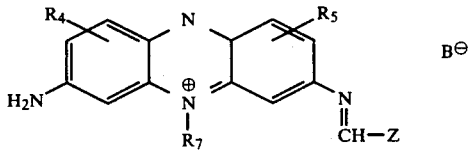
(14)

where $R_4$, $R_5$, $R_7$, Z and B⊖ have the meanings assigned to them above. $R_7$ is e.g. hydrogen, alkyl (of 1 to 4 carbon atoms) or aryl. Preferably $R_7$ is phenyl. An example of such a phenazine compound is the compound of formula

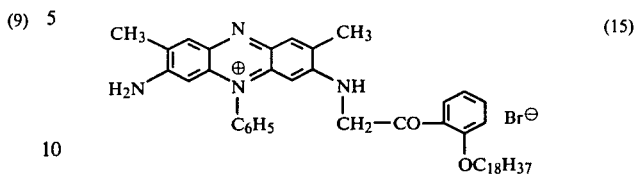
(15)

Compounds of formula (1) wherein X is N and Y is S⊕ are thiazine dyes. Useful thiazine dyes have the formula

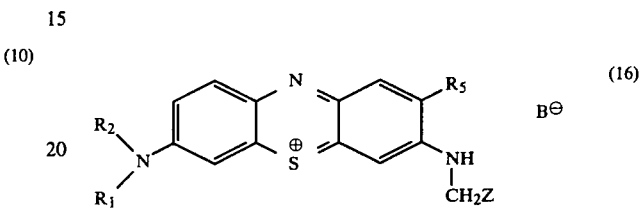
(16)

or when partially oxidised of the formula

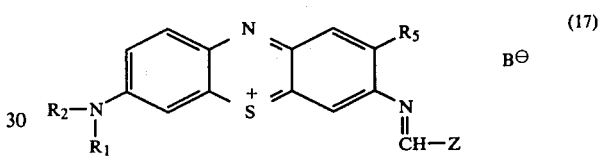
(17)

where $R_1$, $R_2$, $R_5$, Z and B⊖ have the meanings assigned to them above. Preferably $R_5$ is methyl. An example of such a thiazine compound is the compound of formula

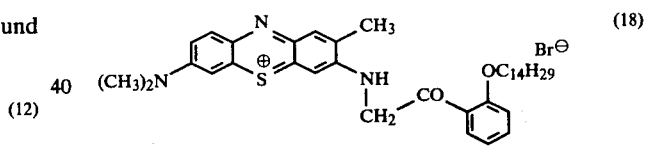
(18)

The dyes of formula (1) and (2) are of use in a process for the production of a photographic image which comprises silver halide development and which includes the step of:

(a) imagewise exposing a photographic assembly which comprises at least during the silver halide developing step, in order, optionally a supercoat layer, at least one silver halide emulsion layer, a dye mordant layer and a support base, there being optionally one or more interlayers between each of the said components and there being associated with the silver halide emulsion layer a compound of general formula (1) or (2), (b) processing the exposed assembly to develop the latent image in the silver halide emulsion layer(s), (c) and simultaneously or subsequently producing an imagewise distribution of a reducing agent which is able to cleave the -NR-CH$_2$ or -N=CH bond in an aqueous medium at a pH less than 3 and reductively cleaving the -NR$_3$-CH$_2$ or -N=CH- bonds of the compound of formula (2) or (1) (whichever is present in the photographic assembly) thereby liberating a diffusible dye imagewise, (d) allowing or causing the diffusible dye to diffuse to the dye mordant layer (e) and there to mordant the dye to form a dye image having a peak absorption within the range 300–800 nm.

The following Examples will serve to illustrate the invention.

EXAMPLE 1

9-Diethylamino-5-(2-octadecyloxyphenacylamino)-benz($\alpha$)-phenoxazin-7-ium bromide (formula (11))

The dye base of Nile Blue A is prepared by reacting an aqueous solution of the dye with sodium carbonate. A mixture of this dye base (1.36 g) and 2-octadecylosyphenacyl bromide (2.02 g) in diethylene-glycol-dimethylether (20 ml) is heated for 4 hours under reflux, and poured into dilute aqueous HCl. The precipitated dyestuff is filtered off, and has a melting point of 56°–58° C.

EXAMPLE 2

9-Diethylamino-5-(4-octadecyloxybenzylidineamino)-benz($\alpha$)-phenoxazin-7-ium chloride (formula (12))

The dye base of Nile Blue A prepared as above (0.32 g) and 4-octadecyloxybenzaldehyde (0.37 g) are heated under reflux diethylene-glycol-dimethylether for 3 hours and poured into dilute aqueous HCl, and the precipitated dyestuff filtered off.

EXAMPLE 3

2,8-Dimethyl-7-dimethylamino-3-(2-octadecyloxyphenacylamino)- phenazin-5-ium bromide (formula (15))

The dye base of Safranin O is prepared by treating an aqueous solution of the dye with sodium carbonate. A solution of this dye base (0.7 g) and 2-octadecyloxyphenacyl bromide (1.04 g) is heated under reflux for 5 hours and added to dilute aqueous hydrochloric acid. The precipitated dyestuff is filtered off.

EXAMPLE 4

7-Dimethylamino-2-methyl-3-(2-tetradecyloxyphenacylamino)-phenothiazin-5-ium bromide (formula (18))

The dye base of Toluidine blue is prepared by treating an aqueous solution of the dye with sodium carbonate. A solution of this dye base (0.75 g) and 2-tetradecyloxyphenacyl bromide (0.75 g) is heated in diethylene-glycoldimethylether under reflux for 5 hours and added to dilute aqueous HCl. The precipitated dyestuff is filtered off, and has a melting point >340° C.

I claim:

1. A compound of the general formula (1)

or of the general formula (2)

wherein X is N, Y is $S^{\oplus}$, $O^{\oplus}$, N or $N^{\oplus}R_7$ where $R_7$ is hydrogen, alkyl of 1 to 4 carbon atoms, phenyl or phenyl substituted by alkyl of 1 to 4 carbon atoms, halogen, hydroxy or carbonyl, $R_1$, $R_2$ and $R_3$ each represent a hydrogen atom or an alkyl group having from 1 to 4 carbon atoms, or $R_1$ and $R_2$ together with the nitrogen atom complete a heterocyclic 5- or 6-membered ring, or one of $R_1$ and $R_2$ can be hydrogen and the other of $R_1$ and $R_2$ can be phenyl, Z is a member selected from the group of the formulae and wherein $R_8$ comprises a ballasting group of at least 10 carbon atoms, and $R_4$ and $R_5$ each represent alkyl of 1 to 4 carbon atoms, amino or halogen or form an annelated benzene ring.

2. A compound according to claim 1 wherein $R_8$ is alkyl or alkoxy of 10 to 24 carbon atoms.

3. A compound according to claim 1 of the formula or when partially oxidised has the formula where $R_1$, $R_2$ and Z have the meanings assigned to them in claim 1 and $B^{\ominus}$ is an anion.

4. A compound according to claim 3, wherein $R_2$ and $R_1$ are methyl or ethyl.

5. A compound according to claim 1 of the formula

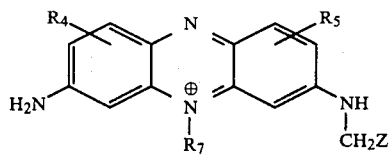

or when partially oxidised of the formula

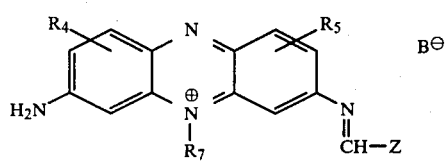

where $R_4$, $R_5$, $R_7$ and Z have the meanings assigned to them in claim 1 and $B^\ominus$ is an anion.

6. A compound according to claim 5 where $R_7$ is phenyl.

7. A compound according to claim 1 of the formula

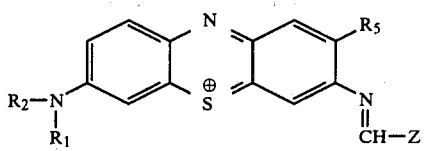

or when partially oxidised of the formula

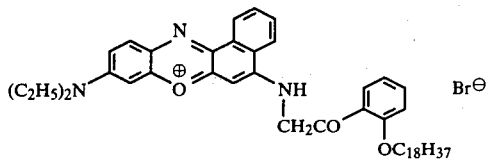

where $R_1$, $R_2$, $R_5$ and Z have the meanings assigned to them in claim 1 and $B^\ominus$ is an anion.

8. A compound according to claim 7, wherein $R_5$ is methyl.

9. A compound of claim 1 having the formula